United States Patent [19]

Valkanas et al.

[11] Patent Number: 5,766,895
[45] Date of Patent: Jun. 16, 1998

[54] METHOD FOR PRODUCTION OF ETHYL ALCOHOL

[75] Inventors: George N. Valkanas; Nicolas P. Valkanas, both of Maroussi; Apostolos G. Vlyssides; Athanassios G. Theodoropoulos, both of Attica, all of Greece

[73] Assignee: Innoval Management Limited, Curacao, Netherlands Antilles

[21] Appl. No.: 676,211

[22] PCT Filed: Sep. 13, 1995

[86] PCT No.: PCT/GR95/00016

§ 371 Date: Jul. 19, 1996

§ 102(e) Date: Jul. 19, 1996

[87] PCT Pub. No.: WO96/08575

PCT Pub. Date: Mar. 21, 1996

[30] Foreign Application Priority Data

Sep. 13, 1994 [GR] Greece ............... 940100423

[51] Int. Cl.⁶ ............... C12P 7/06; C12P 7/08; C12P 7/10
[52] U.S. Cl. ............... 435/161; 435/163; 435/165; 203/19
[58] Field of Search ............... 435/161, 163, 435/165; 203/19

[56] References Cited

U.S. PATENT DOCUMENTS

| | | | |
|---|---|---|---|
| 4,447,534 | 5/1984 | Moebus et al. | 435/161 |
| 4,556,460 | 12/1985 | Robertson et al. | 203/19 |
| 4,696,720 | 9/1987 | Kiser | 203/19 |
| 4,769,112 | 9/1988 | Wheldon | 203/19 |
| 5,035,776 | 7/1991 | Knapp et al. | 203/19 |
| 5,221,357 | 6/1993 | Brink | 127/43 |
| 5,258,293 | 11/1993 | Lynd et al. | 435/165 |
| 5,407,817 | 4/1995 | Lightsey et al. | 435/165 |

*Primary Examiner*—Leon B. Lankford, Jr.
*Assistant Examiner*—Christopher R. Tate
*Attorney, Agent, or Firm*—Birch, Stewart, Kolasch & Birch, LLP

[57] ABSTRACT

The invention describes a method for the economic production of ethyl alcohol involving dehydration of the alcohol in an adsorption-desorption process using ion exchange resins which have been swollen in water from about 50 to 300 times their weight.

5 Claims, No Drawings

METHOD FOR PRODUCTION OF ETHYL ALCOHOL

The invention describes a method for producing ethyl alcohol by fermentation which introduces the following innovations:
- a) Removal of contained water in a process of adsorption-desorption.
- b) Energy self—sufficient production
- c) Plant operation that does not cause any environmental pollution.

More specifically, our invention describes a method for the production of ethyl alcohol by fermentation, in a highly original manner, with no energy consumption and with low production cost. Raw materials to be used are sugars or sugars obtained by hydrolysis of cellulose and pentozanes which are widely found as they are the basic products resulting from the function of metabolism. As such the invention offers an essential solution towards covering basic human necessities.

Today's world is facing a severe problem regarding the availability of raw materials for the production of essential consumer products such as polymers, synthetic products, detergents, and synthetic products for agricultural use. The fast consumption of crude oil reserves which are likely to be depleted within the next 40 years creates potential shortages in the production of such consumer products.

As a result, alternative sources of raw materials are already required, which are not subject to depletion like crude oil. Such a raw material is ethyl alcohol which, if produced on a large scale and at a low cost can satisfy the needs in basic polymer materials, in detergents and synthetic materials. However, the production of ethyl alcohol by fermentation methods from sugars results in 10% aqueous solutions and as a result, dewatering is necessary for its purification. This is effected by successive distillations leading to alcohol strengths of 96%, which constitutes the final azeotropic mixture. To this mixture, benzene is added and after successive distillations pure alcohol is produced. However, such methods are highly energy intensive consuming 20 to 60% more energy compared to what the product can give as a fuel.

Furthermore, during the production of ethyl alcohol by fermentation, a lot of toxic and highly pollutant wastes are produced that can not be handled easily. This problem, along with those mentioned before, make the production of ethyl alcohol by fermentation economically and production wise undesirable. As such fermentation alcohol until now has been used only for the production of alcoholic beverages and is subjected to high taxation making it a very valuable material. Nevertheless, the production of ethyl alcohol by fermentation means has been of great interest for the past 100 years. During the war, for example, ethyl alcohol was produced on a large scale in Germany from lignine cellulosic materials, by their hydrolysis in concentrated hydrochloric acid which was then distilled according to a method known as the Bergius process. In the USA, after the war, the German method was improved by hydrolysing lignine cellulosic materials with sulphuric acid, in the presence of a catalyst and at high temperatures and special conditions, according to a method known as the Scholler-Madison process, but once more this approach was not useful.

In the meantime, in Brazil, mass production of ethyl alcohol as a fuel has been promoted, by making use of the molasses obtained from leaching of sugar canes. The wood like residues known as bagasse are used as fuel during the production, and as a result the external energy requirement is reduced. However, the industrial wastes and the high volume of rejected materials produced, cause severe environmental pollution and since all these are discarded into the Amazon river it is clear that the environmental burden on it is getting very serious.

In the meantime, the EEC is promoting various improvements on these methods. One important achievement is the hydrolysis of cellulose with pure liquid hydrogen fluoride, which is a feasible solution since the hydrolysis is efficient and because the recycling of hydrogen fluoride by distillation has a low energy cost. The inventors, with financial aid from the EEC, have came up with a solution that uses the produced wastes, by digesting them anaerobically in the thermophilic region. By this method, substantial amounts of energy are produced and the environmental pollution problem is effectively tackled.

Following the above and the given the inventors' success in confronting the waste problem by producing useful energy from waste, intense efforts were made, aiming at the mass production of ethanol. The result is a technologically original method by which the production of ethyl alcohol by fermentation is achieved at a low cost and without the creation of environmental pollution.

The inventors have come up with an original and effective solution of biological separation ("biorefining") of lignine cellulosic materials, by which the components of these materials are separated by low cost processes. The result is the separation of lignine cellulosic materials into pentozes, lignine and pure cellulose.

The separation of pentozes is effected through a hydrolysis process, that uses 0.5%–1.0% sulphuric or phosphoric acid as a catalyst, which at temperatures around 90°–130° C. produces pentozes fully hydrolysed into basic sugars. 25–30% w/w of it is obtained and the soft material that is left, which has a high content of cellulose is subjected, further on, to a delignisation process. This is done by simple methods such as with oxygen enriched air, air and alkali or with chlorine, after which lignine and the remaining quantity of pentozes are obtained. Lignine is separated from the mixture easily by precipitating it with an alkali.

The obtained cellulosic mass is then subjected to hydrolysis with hydrogen fluoride in closed circuit where the hydrogen fluoride is continuously distilled and leaves a residue consisting of hydrolysed sugars, principally glucose.

The pentozes obtained from the process of pre-hydrolysis and from the purification of the lignine, are mixed with the glucose that results from the cellulose hydrolysis, and are subjected to fermentation process for the production of ethanol. They represent a quantity that is 70–75% of the original lignine cellulosic material, from which the production of alcohol by means of modern and efficient processes results in alcohol yields around 60%. The invention partially refers to the biological separation (biorefining) of lignocellulosics and in the effective usage of wastes resulting from alcoholic fermentation by anaerobic digestion in the thermophilic region, yielding increased quantities of energy in the form of biogas that contains 85% methane. The alcoholic fermentation and the cellulose hydrolysis by hydrogen fluoride were already known.

In addition to the sugars already mentioned other sugars are used that contain mainly glucose and pentozes such as carrob sirup, molasses, sugarcane hydrolysis residues, sugars from raisins and figs etc. which to date are successfully used for the production of ethanol.

Furthermore, the invention refers in an original and determined manner to the process of alcohol purification from the aqueous solution by the process of adsorption-desorption which is a low cost separation and does not consume energy until pure ethanol is obtained.

We have created products, which are ion-exchange resins proven to be very efficient in separating alcohol from the aqueous solutions, yielding pure ethanol. These products exhibit maximum ion-exchange potential of 5.8–6.0 and are advantageously swollen in water up 300 times their weight. They contain sulfonic groups in high density and as sodium salts they exhibit a large tendency to adsorb water and a relatively low tendency to adsorb ethanol, resulting in complete and effective dewatering of ethanol.

These materials of selective adsorption are polymeric materials, which after special restructuring have acquired a macromolecular chemical structure, characterised by high chemical stability and allows for the introduction of sulfonic groups at high densities in the macromolecular structure with Mc 50. 000. The next stage is to achieve the desorption of water followed by recycling of the adsorbing media. This is simply and originally achieved by creating osmotic conditions which is effected by immersing the materials in the adsorbed stage into a sodium chloride solution of a strength of 3–30%, or by immersing them in sea water, which creates osmotic pressure resulting in the water flowing out fast from the polymeric material which is shrunk in a form that allows for their recycling.

Following the adsorption and consequent desorption of water the following results are achieved as shown in table 1.

TABLE 1

Alcohol losses during the process of adsorption-desorption.

| Adsorption area Ion exchange | 30–60% | 60–90% | 90–100% |
|---|---|---|---|
| | Alcohol losses % potential, | | |
| Swell 200 | | | |
| 5.3 | 1% | 1% | 1.2% |
| 5.5 | 0.6 | 0.7 | 0.8 |
| 5.7 | 0.4 | 0.5 | 0.6 |
| 5.9 | 0.1 | 0.1 | 0.1 |
| 6.0 | 0.08 | 0.07 | 0.07 |
| Swell 100 | | | |
| 5.7 | 0.3 | 3.35 | 0.4 |
| 5.9 | 0.1 | 0.1 | 0.09 |
| 6.0 | 0.008 | 0.01 | 0.01 |

According to the results of table 1 the materials used promote the processes of adsorption and desorption to highly effective and advantageous standards. The production of pure ethanol is achieved and the desorption shows that the alcohol losses, can be negligible within error limits, when perfect conditions prevail regarding ion-exchange rate and swelling degree of the polymer materials. In other words, the invention offers a solution for producing ethyl alcohol from agricultural products and by-products, following their biological separation to their constituent materials and maximisation of the organic mass to be fermented to alcohol. Then the alcohol is separated from the water in an original and effective way. This is done by subjecting the alcohol-water mixture to a adsorption-desorption process, combined with effective usage of the resulting wastes to produce energy in a pollution free manner, so that ethanol is produced on a large scale and at high standards.

The process that the method proposes for the production of ethyl alcohol on a large scale end economically is as follows:

The lignine cellulosic materials, after being processed for biological separation and hydrolysis of cellulose, yield 70–75% fermentable sugars, with lignine isolated representing 15% w/w. Waste materials are produced from unused organic materials in the order of 6–10% and fermentation wastes containing about 30% of organic material based on the total mass. From these waste and organic residue materials, following their anaerobic digestion in the thermophilic region, 20% w/w biogas is produced containing 85% methane and a calorific value of 8,000 kcal/kg which is equivalent to 160,000 kcal/100 kg of cellulosic material. This represents an amount of energy capable of supporting the entire production process of hydrolysing the cellulose, which requires about 20,000 kcal, and for the first distillation of the fermentation broth which separates the waste material yielding an alcohol distillate of 35% in alcohol, which is estimated to require thermal energy in the order of 120,000 kcal.

This alcohol solution is then subjected to the adsorption-desorption process in the system of ion-exchange resins mentioned, at a swelling degree of 200, ion-exchange coefficient of 5.9, which finally yields 99% pure alcohol of excellent quality and purity. The alcohol losses during the process is in the order of 0.1%. The ion-exchange resins following the alcohol-water separation are immersed in a 15% sodium chloride solution or simply in sea water, and by virtue of the osmotic pressure that is produced the adsorbed water is rejected and the resins are obtained in shrunken form ready to be reused.

Alcohol production from plain sugars according to the method is effected in exactly the same way. However, the energy produced from the waste material resulting from its anaerobic digestion, will be capable of covering only the first distillation separating the 35% alcohol and water.

The invention according to its previous description, refers to a complete solution for producing ethanol on a large scale from lignine cellulosic materials or sugars at low cost with complete energy self-sufficiency and without causing environmental pollution. The ethanol that will be produced according to the method can be used as a fuel or as raw material for the production of polymers (e.g polyethylene), detergents, and synthetic raw materials for a multitude of uses and for agricultural applications.

EXAMPLE 1 a. Wheat straws are brought into a tank where the temperature is maintained at 95° C. by the addition of steam. The tank has a capacity of 2 cubic meters and is filled with 1.5 cubic meter of water with a catalyst and 150 kg. of straw. The following catalysts have been used with the respective concentration in water:

| | Catalyst | Concentration |
|---|---|---|
| I | $H_2SO_4$ | 2–3% |
| II | Hcl | 2–3% |
| III | $PO_4H_3$ | 4–6% |

Following heating for three hours, the straws are removed and compressed at 10 atmospheres. The collected liquids have the following sugar content:

I 23.9% II 23.1% III 23%

The remainder solid cellulosic material in a dry condition is:

I 66.1% II 67.1% III 65.2% b. The same process has been applied to pieces of poplar-tree wood of dimensions ranging from 3 to 5 cm. The following results were obtained:

Sugar composition
I 21.2% II 23.4% III 22.8%
Solid Remainder
I 69.3% II 70.5% III 71% c. The same process has been applied to cotton stems. The following results were obtained:
Sugar composition
I 24.1% II 24.8% III 25.3%
Solid Remainder
I 66.4% II 63.8% III 61.9% d. The same process has been applied to rice straw. The following results were obtained:
Sugar composition
I 20.8% II 21.4% III 22.6%
Solid Remainder
I 66.8% II 67.1% III 66.4%

The sugar produced during the processes a-d above are common sugar to an extent of 90–92%. Following further heating of their solution at 100°–120° C. for 1–2 hours, they are totally converted to simple sugar of the following composition:

| | |
|---|---|
| Xylose | 70–75% |
| Arabinose | 10–15% |
| Mannose | 5–6% |
| Lactose | 3–8% |
| Glucose | 5–8% |

The above processes have been carried out at temperatures in excess of 95° C. or at temperatures of 120°–150° C., where lower concentrations of acid catalysts and processing times are required. Furthermore, results obtained are perfect in terms of sugar hydrolysis and quality.

EXAMPLE 2

The cellulosic remainders from example 1 are subjected to a delignisation process in the presence of a) chlorine, b) oxygen, c) atmospheric air.

a. Delignisation in the presence of chlorine
  Yield of cellulosic material: 43–44% (fracture length 6500 m., perforation index: 6, number of bends: 500)
  Yield in Sugar: 8–10%
  Chlorine Absorption: 15–25% w/w b. Delignisation in the presence of oxygen
  Yield of cellulosic material: 43.8% (fracture length 4800 m., perforation index: 5, number of bends: 450)
  Yield in Lignine: 12%
  Yield in Sugar: 16%
  Conditions of processing: NaOH 16%, $MgCO_3$ 1% at 120° C., Oxygen at 5 atm., Flow: 1.8 litters/hour c. Delignisation in the presence of air
  Yield of cellulosic material: 43.4% (fracture length 4750 m., perforation index: 5, number of bends: 440)
  Yield in Lignine: 14%
  Yield in Sugar: 15%
  Conditions of processing: NaOH 16%, $MgCO_3$ 1%, anthraquinone 1%, air pressure=10 atm., Flow: 2.8 litters/hour

EXAMPLE 3

The cellulosic material of example 2 are subjected to hydrolysis with hydrogen fluoride in specially arranged reactors which are defined by the space for the mixing of the cellulosic material with hydrogen fluoride and by the space for the separation of hydrogen fluoride by distillation for recycling.

Five volumes of hydrogen fluoride are added per volume of cellulosic material

One volume of water is also added

The mixing of the cellulosic material with hydrogen fluoride leads to the complete hydrolysis of cellulose. Hydrogen fluoride is recycled by distillation and glucose is collected in an aqueous solution of a glucose concentration of 30–35%.

EXAMPLE 4

Sugars produced as per examples 1, 2 and 3 are subjected to fermentation for alcohol production, according to usual procedures: batch—semi—batch process or continuous process.

Sugars produced as per the examples 1, 2, 3 above are mixed and have a mean composition of:

Pentoze 40–50%, Hectoze 50–60%, mainly Glucose

Alcohol production from sugar of the above composition using modern optimised production processes is in the order of 59–60% w/w.

Total sugar from the various processes of biological separation of lignine cellulosic materials, have the following composition:

a: Glucose 55%, Xylose 31%, Arabinoze 8%, Mannoze 3%, Lactoze 3% b: Glucose 65%, Xylose 16%, Arabinoze 9%, Mannoze 4%, Lactoze 8% c: Glucose 52%, Xylose 33%, Arabinoze 7%, Mannoze 3.5%, Lactoze 4.5%

EXAMPLE 5

The product of fermentation for alcohol production is subjected to distillation for the separation of effluent water and alcohol which is received in the distillate at a concentration of 35%. The effluent water has a high environmental load: BOD 30,000–40,000, COD 60,000–120,000 and suspended organic solids 10–12.%. The effluent water at 80° C. is subjected to anaerobic digestion in the thermophilic region for the production of energy in the form of 0.5 cubic meters of biogas containing methane at a ratio of 85% per kg. COD. The energy generated from the effluents and 5–10% of other organic waste is enough for all energy required for the hydrolysis of cellulose as described in example 3 and for the energy requirements for the distillation of the fermentation product described in this example.

EXAMPLE 6

A 35% alcohol solution is fed to a system of ion exchanging resins which are arranged along a longitudinal column in a manner so that the swelling coefficient of resins at the top of the column is 250, whereas that for resins at the bottom of the column is 50. The resins are selected so as to exhibit a maximum ion exchanging coefficient of 5.9 to 6.5. The length of the column depends on the required result: The product at the end of the column must be pure alcohol, free of any water. When saturated, the column is regenerated simply and quickly by immersion in a solution of sodium chloride of a strength between 3 and 30%, or by immersion in sea water, where due to the osmosis effect, all the adsorbed water flows out and the resins recycled.

Alcohol losses due to adsorption by the resins along with water are negligible, usually in the order of 0.1 to 1%.

We claim:

1. A method for the production of ethanol by fermentation, comprising the steps of:

fermenting a sugar composition to produce a fermentable product containing ethanol;

subjecting said fermentable product to distillation to produce an ethanol solution and waste product;

removing water from the ethanol solution through an adsorption-desorption sequence, wherein ion exchanging resins having an ion exchanging coefficient value of 5.3–6.5 are used to separate ethanol from water, wherein said resins are swollen in water to about 50 to 300 times their weight and adsorb essentially all of the water of the ethanol-water mixture until essentially pure alcohol is produced; and anaerobically digesting said waste product to produce energy sufficient to conduct said method.

2. The method according to claim 1, wherein said sugar composition is obtained from lignine cellulosic materials.

3. A method for the production of ethanol by fermentation, comprising the steps of:

fermenting a sugar composition to produce a fermentable product containing ethanol;

subjecting said fermentable product to distillation to produce an ethanol solution and waste product;

removing water from the ethanol solution through an adsorption-desorption sequence, wherein ion exchanging resins are arranged in a column, where the swell ratio of the resins arranged along the column is gradually reduced from top to bottom, wherein resins at the top of the column have a swell ratio of 250–300 and those at the bottom of the column have a swell ratio of 40–50, wherein water retention is gradually conducted along the column and essentially pure ethanol is collected at the bottom; and anaerobically digesting said waste product to produce energy sufficient to conduct said method.

4. The method according to claim 3, wherein said sugar composition is obtained from lignine cellulosic materials.

5. The method according to claim 1, wherein said ion-exchange resins have maximum ion exchanging coefficient value of 5.8–6.0, and contain sulfonic groups in high density as sodium salts.

* * * * *